US012005089B2

(12) United States Patent
Ensign et al.

(10) Patent No.: US 12,005,089 B2
(45) Date of Patent: Jun. 11, 2024

(54) CVS TRANSPLANTATION FOR TREATMENT OF BACTERIAL VAGINOSIS

(71) Applicant: The Johns Hopkins University, Baltimore, MD (US)

(72) Inventors: Laura Ensign, Towson, MD (US); Richard Cone, Baltimore, MD (US); Justin Hanes, Baltimore, MD (US)

(73) Assignee: THE JOHNS HOPKINS UNIVERSITY, Baltimore, MD (US)

( * ) Notice: Subject to any disclaimer, the term of this patent is extended or adjusted under 35 U.S.C. 154(b) by 258 days.

(21) Appl. No.: 15/174,540

(22) Filed: Jun. 6, 2016

(65) Prior Publication Data

US 2016/0279182 A1   Sep. 29, 2016

Related U.S. Application Data

(63) Continuation-in-part of application No. PCT/US2015/065002, filed on Dec. 10, 2015.

(60) Provisional application No. 62/091,970, filed on Dec. 15, 2014.

(51) Int. Cl.
*A61K 35/747* (2015.01)
*A61K 9/00* (2006.01)
*A61K 9/19* (2006.01)

(52) U.S. Cl.
CPC .............. *A61K 35/747* (2013.01); *A61K 9/00* (2013.01); *A61K 9/0034* (2013.01); *A61K 9/0095* (2013.01); *A61K 9/19* (2013.01)

(58) Field of Classification Search
CPC ...... A61K 35/747; A61K 9/00; A61K 9/0034; A61K 9/0095; A61K 9/19
USPC ...................................................... 424/93.45
See application file for complete search history.

(56) References Cited

U.S. PATENT DOCUMENTS

| | | | |
|---|---|---|---|
| 6,225,356 B1 | 5/2001 | Jones, III | |
| 7,807,440 B2* | 10/2010 | Molin .................... | A23C 9/123 435/252.1 |
| 9,470,676 B2* | 10/2016 | Strgar .................... | G01N 33/50 |
| 10,092,509 B2 | 10/2018 | Maisel | |
| 2003/0118571 A1* | 6/2003 | Reid ...................... | A61K 35/742 424/93.45 |
| 2006/0204484 A1* | 9/2006 | Bisgaard-Frantzen .. | C12N 1/00 424/93.45 |
| 2009/0196844 A1 | 8/2009 | Choi | |
| 2012/0070476 A1* | 3/2012 | Moench ................ | A61K 9/0036 424/400 |
| 2014/0107173 A1 | 4/2014 | Horn | |
| 2014/0163080 A1 | 6/2014 | Horn | |
| 2016/0331792 A1* | 11/2016 | Dominguez-Bello ..................... | A61K 35/742 |

FOREIGN PATENT DOCUMENTS

| | | |
|---|---|---|
| CA | 1072413 | 2/1980 |
| WO | 9427578 | 12/1994 |
| WO | 9918142 | 4/1999 |
| WO | 2009055312 | 4/2009 |
| WO | 2010133761 | 11/2010 |
| WO | 2011049958 | 4/2011 |
| WO | 2013110028 | 7/2013 |
| WO | 2013138343 | 9/2013 |
| WO | 2013138346 | 9/2013 |
| WO | 2014023773 | 2/2014 |
| WO | 2014039185 | 3/2014 |
| WO | 2016025215 | 2/2016 |
| WO | 2016123125 | 8/2016 |

OTHER PUBLICATIONS

Kelly et al. (Tests on Vaginal Discharge. Chapter 179, Clinical Methods: The History, Physical, and Laboratory Examinations, 3rd edition. pp. 833-835).*
Oakley et al. (Diversity of Human Vaginal Bacterial Communities and Associations with Clinically Defined Bacterial Vaginosis. Applied and Environmental Microbiology, Aug. 2008, p. 4898-4909).*
Eckert et al. (Acute Vulvovaginitis. New England Journal of Medicine, 2006, (55):12, 122-1252).*
Ehrstrom et al. (Glucose in vaginal secretions before and after oral glucose tolerance testing in women with and without recurrent vulvovaginal candidiasis. Obstet Gynecol. 2006 108(6) Abstract, pp. 1-2).*
Constanzo et al. (Glucose Concentration Regulates Freeze Tolerance In The Wood Frog Rana Sylvatica. J. exp. Biol. 1993: 181, 245-255) .*
Antonio et al. (The Identification of Vaginal *Lactobacillus* Species and the Demographic and Microbiologic Characteristics of Women Colonized by These Species. The Journal of Infectious Diseases 1999; 180: 1950-6).*
Siaterilis et al. (Effect of culture medium and cryoprotectants on the growth and survival of probiotic lactobacilli during freeze drying. Letters in Applied Microbiology 48 (2009) 295-301).*

(Continued)

*Primary Examiner* — Sharmila G Landau
*Assistant Examiner* — Natalie M Moss
(74) *Attorney, Agent, or Firm* — PABST PATENT GROUP LLP

(57) ABSTRACT

Methods and materials for treating bacterial vaginosis ("BV") are provided. Cervicovaginal secretions ("CVS") from a woman with vaginal microbiota dominated (>50%) by one of the species of *lactobacillus* typically found in the human vagina, e.g. *Lactobacillus crispatus, L. iners, L. gasseri, L jensenii*, is transplanted to women with BV as a method for restoring beneficial vaginal microbial communities and/or increasing resistance to sexually transmitted disease. Efficacy can be enhanced, or the properties of the endogenous CVS improved, through administration of an acidifying agent such as lactic acid. The examples demonstrate the role of healthy CVS in disease resistance, and the effect of pH on CVS properties. The examples also describe the collection and transplantation of healthy beneficial CVS into women at risk for, or after treatment for, BV.

11 Claims, 4 Drawing Sheets

(56) References Cited

OTHER PUBLICATIONS

Lewis et al. (Degradation, Foraging, and Depletion of Mucus Sialoglycans by the Vagina-adapted Actinobacterium Gardnerella vaginalis. The Journal Of Biological Chemistry vol. 288, No. 17, pp. 12067-12079, 2013).*
Eschenbach et al. (Infectious Vaginitis. 2008 pp. 1-33).*
Antonio, et al., "Vaginal colonization by probiotic Lactobacillus crispatus CTV-05 is decreased by sexual activity and endogenous Lactobacilli", J Infectious Dis., 199 (10);1506-13 (2009).
Criswell, et al.,, "Haemophilus vaginalis: vaginitis by inoculation from culture" Obstet and Gynecol., 33(2) 195-199 (1968).
Gajer, et al., "Temporal dynamics of the human vaginal microbiota" , Sci Transl Med., 4(132) 132ra52 (2012).
Ghartey, et al., "Lactobacillus crispatus dominant vaginal microbiome is associated with inhibitory activity of female geneital tract secretions against escherichia coli" , Plos One, 9(5):1-8 (2014).
Hess, et al., "Results of Fortification Rapid Assessment Tool (FRAT) surveys in sub-Saharan Africa and suggestions for future modifications of the survey instrument" , Food and Nutrition Bull., 34(1):21-38 (2013).
Larsson and Forsum, "Bacterial vaginosis—a disturbed bacterial flora and treatment enigma" , APMIS. 113: 305-16 (2005).
Marrazzo, et al,. "Characterization of vaginal flora and bacterial vaginosis in women who have sex with women" , J Infect Dis.,, 185:1307-13 (2002).
Mirmonsef, et al., "Free glycogen in vaginal fluids is associated with lactobacillus colonization and low viginal pH" , Plos One, 9(7);1-11 (2014).
Nugent, et al., "Reliability of diagnosing bacterial vaginosis is improved by a standardized method of gram stain interpretation" , J Clin Microbiol., 29(2):297-301 (1991).
Price, et al., "Community Analysis of Chronic Wound Bacteria Using 16S rRNA Gene-Based Pyrosequencing: Impact of Diabetes and Antibiotics on Chronic Wound Microbiota" , Plos One,4(1):1-10 (2009).
Ravel, et al., "Vaginal microbiome of reproductive-age women" , PNAS, 108 (Supp1):4680-7 (2011).
Romero, et al.,, "The composition and stability of the vaginal microbiota of normal pregnant women is different from that of non-pregnant women" , Microbiome, 2(1):4, (2014).
Verstraelen, et al., "Longitudinal analysis of the vaginal microflora in pregnancy suggests that L. crispatus promotes the stability of the normal vaginal microflora and that L. gasseri and/or L. iners are more conducive to the occurrence of abnormal vaginal microflo" , BMC Microbiol. ;9:116, doi: 10.1186/1471-2180-9-116 (2009).
Xu, et al., "Antagonistic potential against pathogenic microorganisms and hydrogen peroxide production of indigenous lactobacilli isolated from vagina of Chinese pregnant women" , Biomed Enviro Sci., 21(5):365-71 (2008).
Zhou, et al., "Vaginal microbiota of women with frequent vulvovaginal candidiasis" , Infection Immunity, 77(9):4130-5 (2009).
International Search Report for PCT/US2015/065002 dated Mar. 11, 2016.
Antonio, et al., "DNA Fingerprinting of Lactobacillus crispatus Strain CTV-05 by Repetitive Element Sequence-Based PCR Analysis in a Pilot Study of Vaginal Colonization", J Clinic Microbiol., 41(5):1881-7 (2003).
Czaja, et al., "Phase I Trial of a Lactobacillus crispatus Vaginal Suppository for Prevention of Recurrent Urinary Tract Infection inWomen", Infect Dis Obstetrics Gynecolog, Article ID 35387, 8 pages (2007).
Hayashi, et al., A Single Strain of Clostridium butyricum Induces Intestinal IL-10-Producing Macrophages to Suppress Acute Experimental Colitis in Mice, Cell Host Microbe, 13:711-22 (2013).
Hemmerling, et al., "Phase 1 Dose-ranging Safety Trial of Lactobacillus crispatus CTV-05 (Lactin-V) for the Prevention of Bacterial Vaginosis", Sex Transm Dis., 36(9):564-9 (2009).
Hemmerling, et al., "Phase 2a Study Assessing Colonization Efficiency, Safety, and Acceptability of Lactobacillus crispatus CTV-05 in Women With Bacterial Vaginosis", Sex Transm Dis., 37(12): 745-50 (2010).
Imase, et al., "Efficacy of Clostridium butyricum preparation concomitantly with Helicobacter pylori eradication therapy in relation to changes in the intestinal microbiota", Microbiol Immuno., 52:156-61 (2008).
Jhu and Tolar, Baltimore HIV scholar: HIV & nanomedicine. New & Events, http://hopkinscfar.org/news-events/news/P195/news.detail/hiv-nanomedicine, Aug. 14, 2014.
Kanai, et al., "A breakthrough in probiotics: Clostridium butyricum regulates gut homeostasis and anti-inflammatory response in inflammatory bowel disease", J Gastroenterol., 50:928-39 (2015).
Kashiwagi, et al., "Smad2 and Smad3 Inversely Regulate TGF-b Autoinduction in Clostridium butyricum-Activated Dendritic Cells", Immunity, 43:65-79 (2015).
Neu, et al., "Cesarean versus vaginal delivery: Long term infant outcomes and the hygiene hypothesis", Clin Perinatol., 38(2):321-31 (2011).
Ngugi, "Effects of BV-Associated Bacteria and Sexual Intercourse on Vaginal Colonization with the Probiotic Lactobacillus crispatus CTV-05", Sex Transm Dis . 38(11):1020-7 (2011).
Pollan, "Some of my best friends are germs", The New York Times Magazine, 17 pages, May 15, 2013.
Sato, et al., "Effects of Probiotics on Serum Bile Acids in Patients With Ulcerative Colitis", Hepatogastroenterology. 59(118): 1804-8 AGA Abstracts (2012).
Shimbo, et al., , "Effect of Clostridium butyricum on fecal flora in Helicobacter pylori eradication therapy", World J Gastroenterol, 11(47):7520-4 (2005).
Shinnoh, et al,. "Clostridium butyricum MIYAIRI 588 shows antitumor effects by enhancing the release of TRAIL from neutrophils through MMP-8", Intl J Oncol., 42:903-11 (2013).
Stapleton, et al., "Randomized, Placebo-Controlled Phase 2 Trial of a Lactobacillus crispatus Probiotic Given Intravaginally for Prevention of Recurrent Urinary Tract Infection", CID, 52:1212-7 (2011).
Takahashi, et al., , et al., "The effect of probiotic treatment with Clostridium butyricum on enterohemorrhagic *Escherichia coli* O157:H7 infection in mice", FEMS Immunol Med Microbiol., 41:219-26 (2004).
Witkin, et al., "HIV inhibition by lactobacilli: Easier in a test tube than in real life", MBio, 6(5): ): e01485-15 (2015).
Woo, et al., "Inhibition of the cytotoxic effect of Clostridium difficile in vitro by Clostridium butyricum MIYAIRI 588 strain", J Med Microbiol., 60:1617-25 (2011).
Moebus, et al., "Alginate-poloxamer microparticles for controlled drug delivery to mucosal tissue", European Journal of Pharm. and Biopharm., 72:42-53 (2009).
Cynkowska, et al., "Novel antiglaucoma prodrugs and codrugs of ethacrynic acid", Bioorganic Med Chem Ltrs., 15(15):3524-7 (2005).
Date, et al., "Development and evaluation of a thermosensitive vaginal gel containing raltegravir + efavirenz loaded nanoparticles for HIV prophylaxis,", Antiviral Res., 96:430 (2012).
Ensign-Hodges, "Mucus-Penetrating Nanoparticles for Vaginal and Gastrointestinal Drug Delivery", dissertation, Johns Hopkins University (2012).
Gelperina, et al., "Drug delivery to the brain using surfactant-coated poly (lactide-co-glycolide) nanoparticles: influence of the formulation parameters," European Journal of Pharmaceutics and Biopharmaceuticals, 74(2):157-163 (2010).
International Search Report for PCT/US2015/017120 dated May 29, 2015.
International Search Report for PCT/US2016/013914 dated Apr. 14, 2016.
International Search Report for PCT/US2016/014956 dated Apr. 22, 2016.
International Search Report for PCT/US2017/036154 dated Aug. 28, 2017.
Lisco, "Acyclovir Is Activated Into A HIV-1 Reverse Transcriptase Inhibitor In Herpesvirus-Infected Human Tissues", Cell Host & Microbe, 4:260 (2008).

(56) References Cited

OTHER PUBLICATIONS

Na, et al., "Menadione and ethacrynic acid inhibit the hypoxia-inducible factor (HIF) pathway by disrupting HIF-I[alpha] interaction with". Biochemical and Biophysical Research Communications, 434(4): 879-884 (2013).
Nirmal, et al., "In-Situ gel: New trends in Controlled and Sustained Drug Delivery System", International Journal of PharmTech Research, 2(2):1398-1408 (2010).
Zhang et al: "pH-responsive 1-15 nanoparticles releasing tenofovir intended for the prevention of HIV transmission", European Journal of Pharmaceuti CS and Biopharmaceutics, 79(3): 526-536 (2011).
Liu, et al. "Developments of mucus penetrating nanoparticles", Asian journal of Pharmaceutical Sciences, 10(4):275-82 (2015).
Maisel, et al., "Enema ion compositions for enhancing colorectal drug delivery", Journal of Controlled Release, 209:280-7 (2015).

\* cited by examiner

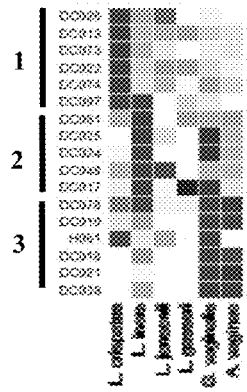 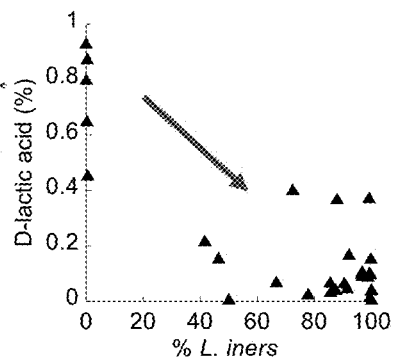 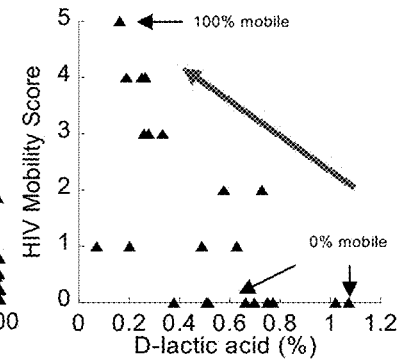
FIG. 2A          FIG. 2B          FIG. 2C
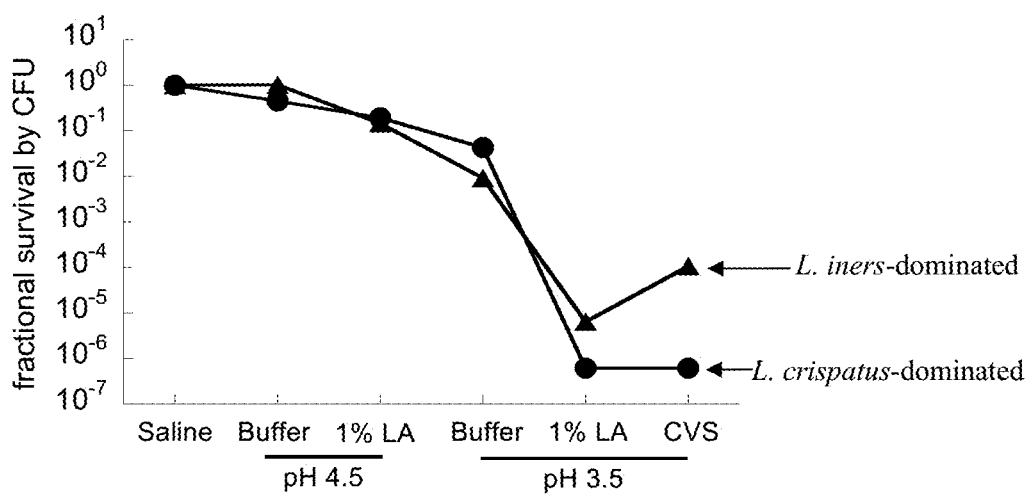
FIG. 3

CVS TRANSPLANTATION FOR TREATMENT OF BACTERIAL VAGINOSIS

CROSS REFERENCE TO RELATED APPLICATIONS

This application is a continuation-in-part of International Application no. PCT/US2015/065002, filed on Dec. 10, 2015, which claims priority to and benefit of U.S. Provisional Application No. 62/091,970 "CVS Transplantation for Treatment of Bacterial Vaginosis" filed on Dec. 15, 2014, the disclosures of which are hereby incorporated herein by reference in their entirety.

STATEMENT REGARDING FEDERALLY SPONSORED RESEARCH OR DEVELOPMENT

This invention was made with Government Support under NIH grants R01HD062844, R21/R33A1094519, and R21/R33A1079740 by the National Institutes of Health. The Government has certain rights in the invention.

FIELD OF THE INVENTION

The present invention is generally in the field of treatment of infections of the vagina and sexually transmitted diseases.

BACKGROUND OF THE INVENTION

Approximately one-third of all women currently have bacterial vaginosis (BV), a condition where the vaginal microbiota is not dominated by lactobacilli. Another one-third of women have mixed vaginal microbiota ("intermediate BV"), and only one-third of women have healthy, lactobacilli-dominated microbiota. Women with BV are known to have >2-6-fold increased susceptibility to numerous sexually transmitted infections (STI), including HIV, herpes (HSV), gonorrhea, chlamydia, and other viral, bacterial, and protozoan pathogens. STI transmission rates from women to men are higher if the woman has BV. Pregnant women with BV are much more susceptible to miscarriage, premature delivery, and post-partum endometriosis. Strong links have also been established between BV and increased incidence of pelvic inflammatory disease and urinary tract infections.

Perhaps most alarming, few people have heard of BV, and even fewer know how to identify if they have it. The standard of care is vaginal or oral antibiotics. However, the effectiveness of antibiotics is limited by mutation leading to antibiotic-resistance, and estimates of BV relapse 4 weeks after antibiotic treatment are as high as 70%. Although BV is an incredibly important global women's health issue, there is currently no known long-term cure. Several attempts have been made to colonize the vagina with large doses of specific probiotic strains of lactobacilli, but the results have been disappointingly modest. In contrast to probiotic strategies in which a single strain of dormant lactobacilli is placed into an environment that is detrimental to its survival, isolating one important player in a complex mix of factors appears to be too simplistic of an approach to be fully effective.

Studies have been conducted involving the introduction of probiotic *lactobacillus* strains in isolation, which have demonstrated modest results. One strain in particular, *Lactobacillus crispatus* CTV-05, has been demonstrated to achieve colonization in the vaginas of women without BV and was demonstrated as safe and tolerable in a Phase 2 trial in women with BV. Fecal transplants have been demonstrated to be safe, and have had as high as 94% effectiveness at eradicating *C. difficile* infection in clinical studies. Probiotic products have also been used, as reported by Antonio MA, et al. J Infectious Dis 199(10); 1506-1513 (2009), who studied microbial composition over time, and demonstrates that pregnant women that have healthy, term pregnancies are more likely to have *Lactobacillus crispatus*-dominated microbiota, and their microbial communities are more stable over time. Romero et al. Microbiome, 2:4 http://www.microbiomejournal.com/content/2/1/4 (2014) was the first report of the temporal dynamics of vaginal microbiota in healthy, reproductive age women. This paper discusses that *Lactobacillus crispatus* dominated communities are more stable, and therefore, less often associated with transitions to a state of bacterial vaginosis (BV). Gajer et al. Science Translational Medicine, 4(132) 132ra52 (2012) demonstrated in pregnant women that *L. crispatus* colonization is more stable, and that *L. iners* is more conducive to the development of BV. Verstraelen et al. BMC Microbiology 9(116) (2009) describes the first, and now unethical, studies of BV-associated bacteria, with pregnant women. *Gardnerella vaginalis* alone was insufficient in initiating BV in 12 out of 13 women with *lactobacillus*-dominated vaginal microbiota. However, 11 of 15 women inoculated with cervicovaginal fluid from women infected with *G. vaginalis* developed symptoms, indicating that other environmental factors were needed for the bacteria to thrive. Criswell et al. Obstet and Gynecol. 33(2) 195-199 (1968) describes the prevalence of BV amongst women who have sex with women. They found that of 58 monogamous couples, 95% were concordant for the presence or absence of BV, which was statistically very distinct from the normal distribution expected in the female population. This would indicate that vaginal microbiota transfer must occur as a result of transfer of vaginal fluids. Marrazzo et al. JID. 185:1307-13 (2002) described BV relapse rates of up to 70% one month after antibiotic treatment. See also Larsson and Forsum, APMIS. 113: 305-16 (2005).

The introduction of beneficial bacterial communities within the environmental milieu that supports their survival appears to be more effective than introducing isolated bacterial strains. No such communities have been identified or tested for treatment of BV, however.

It is therefore an object of the present invention to provide a method and materials for treating BV.

It is another object of the present invention to identify "donor" participants with the characteristics necessary for providing donor samples for treatment and prevention of BV.

It is another object of the present invention to provide methods and materials for CVS transplants to increase the effectiveness of standard antibiotic treatments for treating bacterial vaginosis.

SUMMARY OF THE INVENTION

Method and materials for treating bacterial vaginosis (BV) are disclosed herein. Methods and materials for transplanting cervicovaginal secretions ("CVS") to increase the effectiveness of standard antibiotic treatments for BV are also described. Methods for identifying "donor" participants with the characteristics necessary for providing donor samples for treatment and prevention of BV have also been developed.

Instead of isolating and purifying a particular strain, CVS from one or more women with vaginal microbiota dominated (>50%) by species typically found in the human vagina, e.g. *Lactobacillus crispatus, Lactobacillus iners, Lactobacillus gasseri, Lactobacillus jensenii*, is transplanted to women with BV as a method for restoring beneficial vaginal microbial communities and/or increasing resistance to sexually transmitted disease and BV recurrence. Efficacy can be enhanced, or the properties of the endogenous CVS improved, through administration of an acidifying agent, before and/or after transplantation, such as lactic acid. The CVS can also be filtered for sterility and to remove particles, aggregates and cells, for administration as a filtrate, and optionally mixed with isolated and cultured *Lactobacillus* bacteria, or spray dried or lyophilized and, optionally, packaged into single dosage unit applicators.

The method is based on the following:

Only certain *lactobacillus* communities and strains are truly healthy and protective against vaginal infection and should be transplanted to women after treatment for bacterial vaginosis.

The whole bacterial communities must be introduced in the vaginal environment to establish colonization, rather than isolated bacterial strains.

Components of cervicovaginal mucus itself are beneficial to bacterial growth and survival, indicating that the mucus itself is the ideal vehicle for introduction of microbiota into the vagina.

Vaginal microbiota transplantation can be supported by repeated vaginal delivery of lactic acid or other similar compounds.

Examples demonstrate the role of healthy CVS in disease resistance, and the effect of pH on CVS properties. The examples also describe the collection and transplantation of healthy beneficial CVS into women at risk for, or after treatment for, BV.

BRIEF DESCRIPTION OF THE DRAWINGS

FIGS. 2A-2C are graphs. FIG. 2A is an abbreviated heat map showing relative abundance of select bacterial species in CVS samples: group 1: *L. crispatus*-dominated; group 2: *L. iners* dominated; group 3: BV samples. FIG. 2B is a plot illustrating that the percentage of D-lactic acid in CVS decreases as the percentage of *L. iners* (calculated in A) increases. FIG. 2C is a plot demonstrating that HIV mobility (score of 5=100% mobility, score of 0=0% mobility) increases as the amount of D-lactic acid decreases.

FIG. 3 is a graph of the survival of BV-associated bacteria in BV-CVS. Treatment with buffer or 1% lactic acid (LA) at pH 4.5 has minimal effect on BV-associated bacteria. In contrast, 1% LA at pH 3.5 (mimicking the healthy vagina) or the supernatant of a healthy *L. crispatus*-dominated CVS sample, resulted in 5-log reduction in BV-associated bacteria survival. In contrast, the *L. iners*-dominated CVS sample was far less effective (only ~2-log reduction) at killing BV-associated bacteria in BV-CVS, and less effective than 1% LA alone.

DETAILED DESCRIPTION OF THE INVENTION

I. Definitions

Figure 1A:
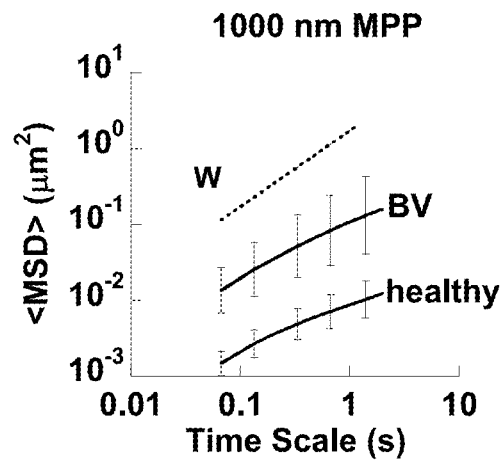
FIGS. 1A and 1B are graphs of the ensemble-averaged geometric mean square displacements (<MSD>) as a function of time scale for (A) 1000 nm MPP (carboxylate-modified polystyrene nanoparticles with 2 kDa polyethylene glycol chemical conjugated to the surface to produce a mucoinert surface coating), which diffuse similarly in CVS from women with healthy vaginal microbiota and from women with BV (FIG. 1A), and (B) HIV, which diffuses rapidly in BV CVS, but is immediately trapped in CVS from women with healthy microflora (FIG. 1B). W=diffusion rate in water.

Probiotic, as used herein, utilizes the World Health Organization's 2001 definition of "live micro-organisms which, when administered in adequate amounts, confer a health benefit on the host". Probiotics must be alive when administered, have viability and reproducibility based on in vivo testing, and during use and storage.

Microbial flora refers to the microorganisms that normally live in the gastrointestinal tract, skin, nose, etc. In a healthy human, the internal tissues, e.g. blood, brain, muscle, etc., are normally free of microorganisms. However, the surface tissues, i.e., skin and mucous membranes, are constantly in contact with environmental organisms and become readily colonized by various microbial species. The mixture of organisms regularly found at any anatomical site is referred to as the normal flora, except by researchers in the field who prefer the term "indigenous microbiota". Bacteria are the most numerous microbial components of the normal flora.

Microbiota, a term created by Jeffrey Gordon, refers to the collection of microbial species that form a microbial community. This includes the normal flora and "harmful" ones. "Microbiome," refers to the collection of genes present in the genomes of microbial species present in a community.

Bacterial vaginosis ("By"), as used herein, refers to the overgrowth of one of several non-*Lactobacillus* types of bacteria normally present in the vagina, upsetting the natural balance of vaginal bacteria.

Cervicovaginal secretions refers to the mixture of mucus secreted by the cervix, shed epithelial cells, vaginal transudate, and bacteria found in the vagina of a woman.

Sexually transmitted diseases ("STD") are any of various diseases or infections (such as syphilis, gonorrhea, chlamydia, and genital herpes) that are usually transmitted by direct sexual contact and include some (as hepatitis B and AIDS) that may be contracted by other than sexual means.

As used herein, a "dissolution agent" is an acid, or salt thereof, that is added to the vaginal area, vaginal secretions, cervicovaginal secretions, or formulations containing cervicovaginal secretions. The secretions may be in dry (lyophilized) or wet form.

Cryoprotectant is any agent that prevents the formation of ice crystals, which can rupture cell membranes.

Diluent is any solution, optionally containing a cryoprotectant and/or a dissolution agent. Diluent may optionally be balanced for a desired osmolarity.

II. Formulations for Treatment of BV

A. CVS Transplants

The materials for transplant are secretions collected using standard techniques from women with vaginal microbiota dominated (>50%) by species of *lactobacillus* typically found in the human vagina, e.g. *Lactobacillus crispatus, Lactobacillus iners, Lactobacillus gasseri, Lactobacillus jensenii*, who are healthy, free of sexually transmitted disease and bacterial vaginosis, and have a low pH in the secretions. As described in Example 1, these can be collected using commercially available materials such as Instead Soft Cup menstrual fluid device, beaker, syringe, or absorbent matrix.

The secretions are preferably stored in the refrigerator at 4° C. for up to 1 week, or in certain cases, immediately frozen after collection and stored for up to several months, before being implanted into the recipient. Samples must maintain at least 20% viable bacteria prior to use.

The identity and relative abundance of bacteria in the CVS are determined by 16S rRNA pyrosequencing. The sequencing data is then used to identify a community state, and only samples classified within the community states of *lactobacillus* that are typically found in the human vagina, including *Lactobacillus crispatus, Lactobacillus iners, Lactobacillus gasseri*, and *Lactobacillus jensenii*, will be considered for transplant. This community state often includes other species of *Lactobacillus* in smaller fractions. Genetic sequencing techniques and assignment of community states have been defined by the laboratory of Jacques Ravel at the University of Maryland.

B. Additives: Dissolution Agents, Cryoprotectants and Diluents

The secretions may be in dry (lyophilized) or wet form. Suitable dissolution agents include nitrogen-free organic acid having at least one carboxylic acid group and a total of from 2 to about 20 carbon atoms, a phosphoric acid containing compound, a sulfonated polyphosphoric acid compound, a polyphosphonate having three or more phosphonate groups, an enzyme; or salts thereof; or combinations thereof. Examples include lactic acid, citric acid, tartaric acid, gluconic acid, glycolic acid, hydroxysuccinic acid, galactaric acid, hydroxypropionic acid, lactic acid, glyceric acid, hydroxybutyric acid, hydroxyisobutyric acid, hydroxy methylbutyric acid, bis(hydroxymethyl) propionic acid, gibberellic acid, hydroxyoctadecanoic acid, di-tert-butyl hydroxybenzoic acid, benzilic acid, hydroxyl fluorenecarboxylic acid, hydroxydecanoic acid, hydroxynaphthalenecarboxylic acid, hydroxybenzenedicarboxylic acid, hydroxymethylbenzoic acid, hydroxyphenylacetic acid, mandelic acid, hydroxymethoxybenzoic acid, methoxysalicylic acid, hydroxyoctanoic acid, hydroxy cinnamic acid, dihydroxycinnamic acid, dihydroxy-hydrocinnamic acid, hydroxyphenylpropionic acid, dihydroxytartaric acid, hydroxymethoxycinnamic acid, chlorohydroxybenzoic acid, chloromandelic acid, chloro phthalic acid, salicylic acid, chlorosalicylic acid, citrazinic acid, dibromo hydroxybenzoic acid, dichlorohydroxy-benzoic acid, dichlorosalicylic acid, galactouronic acid, glucuronic acid, hydroxypropanedioic acid, hydroxyphenyl propionic acid, lactic acid, methoxysalicylic acid, trihydroxybenzoic acid, or their partial salts and combinations thereof. Another group of organic acids are various hydroxyl free and nitrogen free saturated or unsaturated dicarboxylic acids having from 2 to about 20 carbon atoms and can contain nitrogen atoms. Examples include oxalic acid, malonic acid, succinic acid, glutaric acid, adipic acid, pimelic acid, maleic acid, fumaric acid, decanedoic acid, camphoric acid, benzenedicarboxylic acid, phthalic acid, cyclohexanedicarboxylic acid, cyclohexanediacetic acid, octanedioc acid, homophthalic acid, phenylmalonic acid, cyclopentanediacetic acid, nonanedioic acid, benzylmalonic acid, phenylenediacetic acid, phenylsuccinic acid, bromosuccinic acid, carboxyphenacetic acid, cyclobutanedicarboxylic acid, cyclohexanedicarboxylic acid, decanedicarboxylic acid, dibromosuccinic acid, dichlorophthalic acid, diethylmalonic acid, diglycolic acid, dimethylmalonic acid, dimethyl pentanedioic acid, dimethylsuccinic acid, ethylmalonic acid, glutamic acid, hexenedioic acid, imino diacetic acid, methylmalonic acid, methylsuccinic acid, naphthalene dicarboxylic acid, oxalacetic acid, oxopentanedioic acid, undecane dicarboxylic acid, dipicolinic acid, or their partial salts, and combinations thereof.

Cryoprotectant is any agent that prevents the formation of ice crystals, which can rupture cell membranes. Cryoprotectants include extracellur cryoprotectants that do not penetrate bacterial cell walls, and intracellular cryoprotectants that penetrate bacterial cell walls. Examples of extracellular cryoprotectants include sucrose, dextrose and polyvinylpyrrolidone (PVP). Examples of intracellular cryoprotectants include dimethyl sulfoxide (DMSO) glycerol (glycerine).

Diluent is any solution, optionally containing a cryoprotectant and/or a dissolution agent. Diluent may optionally be balanced for a desired osmolarity. Exemplary diluent may be a solution of sodium chloride and lactic acid.

In a preferred embodiment, the recipient may also receive daily vaginal treatment with a food acid such as a lactic acid gel, spray or powder before and/or after transplantation to encourage *Lactobacillus* growth. Daily treatment may occur for up to 1 week before and/or after transplantation. The preferred concentration range of lactic acid to promote *Lactobacillus* survival is 1-1.5% lactic acid. Lactic acid is preferred to other types of food acid such as vinegar, lemon juice, and acetic acid, although these may also be utilized.

III. Methods of Treatment

A. Treatment of BV

Certain types of *lactobacillus* and compositions of vaginal microbial communities confer stability and resistance to bacterial vaginosis (BV). These are preferably obtained from women with vaginal microbiota dominated (>50%) by species of *lactobacillus* typically found in the human vagina, e.g. *Lactobacillus crispatus, Lactobacillus iners, Lactobacillus gasseri, Lactobacillus jensenii*, who are healthy, free of sexually transmitted disease and bacterial vaginosis, and have a low pH in the secretions. These are administered to women with BV, as identified clinically with Amsel's criteria, and confirmed in the laboratory by Nugent scoring (Nugent et al., *Journal of Clinical Microbiology*, 29(2):297-301 (1991)). In a preferred embodiment, women with recurrent BV (requiring >3 treatment courses in 1 year) will first be treated with standard antibiotic treatment to reduce the bacterial load in the vagina. Twenty-four hours after the final antibiotic dose, the recipient will then receive a CVS transplant. The recipient will remain supine for at least 1 hour. Vaginal swabs will be collected from the recipient before transplant, after transplant, and at standard intervals (1 month, 2 months) after transplant. Characterization of vaginal microbiota will be done by 1) Amsel's criteria, 2) Nugent score, and 3) 16S rRNA sequencing. "Success" will be defined as a lack of BV relapse at 1 and 2 months after transplant, as assessed by Amsel's criteria and Nugent score. 16S rRNA sequencing will reveal the relative abundance of vaginal bacteria, and the degree of similarity to the composition of the transplanted sample.

B. Increased Resistance to STDs

CVS transplants also have barrier properties to sexually transmitted pathogens such as HIV are compromised in BV. However, these mucus barrier properties do not appear to be restored, even after successful antibiotic treatment, which is likely because the *lactobacillus* species most commonly associated with BV (strains of *L. iners*) also have a negative impact on the vaginal mucus barrier. Transplantation of more beneficial *lactobacillus* types, including the vaginal microbial community and the mucus environment in which they live, is a promising method for re-establishing healthy bacterial communities that do not compromise the structural and adhesive properties of CVS in the vaginas of women with recurrent BV.

Several samples have been obtained with high Nugent scores and pH>4.5 (together indicating BV) which look normal to the naked eye or are very thick in consistency, which may be a further reflection of the diversity of BV-associated microbiota and their effects on CVS. Changes in the local microstructure of BV samples, as probed by 1000 nm mucus penetrating particles (MPP) (FIG. 1A), revealed a relative degradation of the CVS structure in BV. Additionally, due to the high pH (>4.5) of BV-CVS, HIV diffuses rapidly in BV-CVS (FIG. 1B). BV-CVS has a similar lack of barrier properties to HSV. The effectiveness of treatment for BV and the barrier properties of CVS change after treatment with antibiotics. HIV rapidly diffused in CVS from women after antibiotic treatment, despite BV symptom (pH, consistency, odor) resolution, indicating that women that have ever been treated for BV may have increased susceptibility to STIs.

Although the CVS samples were acidic after treatment, it was found that the L/D lactic acid ratios were similar to when the participants had BV. This further supports the belief that certain strains of *L. iners*, the type of lactobacilli most commonly present in the vagina after BV treatment, may not be associated with increased protective benefits in the vagina.

C. Dosage Unit Formulations

The CVS or a sterile filtered and pH adjusted CVS can be packaged into single dosage units for ease of administration. Typically these would be in a dispenser or applicator, sterile packaged, which has a tip for insertion into the vagina, and a plunger to expel the packaged formulation.

In other embodiments, the CVS can be lyophilized or spray dried and stored frozen or in a sterile container, for resuspension immediately prior to use. The CVS can be resuspended with sterile water, a weak acidic solution, gel, or buffer.

In yet another embodiment, the spray dried formulation can be formulated as a disk or wafer, which is inserted into the vagina where it hydrates and repopulates the vaginal mucosa.

In all of these embodiments, dyes, perfumes, pH buffering agents, drying or resuspending agents, or other materials standard in the probiotic field can be incorporated into the formulations.

Typically, the dosage unit formulations contain between $10^3$ and $10^{15}$ colony forming units (CFU) of any one of *Lactobacillus crispatus, Lactobacillus iners, Lactobacillus gasseri, Lactobacillus jensenii*. In some aspects, the dosage units provide between $10^3$ and $10^{15}$ CFU of any combination of *Lactobacillus crispatus, Lactobacillus iners, Lactobacillus gasseri, Lactobacillus jensenii*.

The present invention will be further understood by reference to the following examples.

Example 1: Characterization of Mobility Differences in Normal and BV Vaginal Mucosa For CVS transplants to be successful, bacteria in the "donor" sample must be in an environment that is beneficial to their survival. Lactobacilli thrive in an acidic environment with high lactic acid concentration, which is inhospitable to many other types of bacteria, including those commonly associated with BV. Thus, it is important that, upon mixing with the vaginal secretions of a woman with BV, the environment must become acidified.

Materials and Methods

Ensemble-averaged geometric mean square displacements (<MSD>) as a function of time scale for 1000 nm MPP, which diffuse more rapidly in CVS from women with BV than from women with healthy microbiota, and for HIV, were measured in BV-CVS as well as in CVS from women with healthy microbiota (not on hormonal contraceptives). W=theoretical MPP/HIV diffusion rate in water.

The Percentage of HIV with $Log_{10}$ (MSD) values at a time scale of 1 s in CVS from women collected before and after antibiotic treatment for BV were calculated.

Results

Figure 1B:
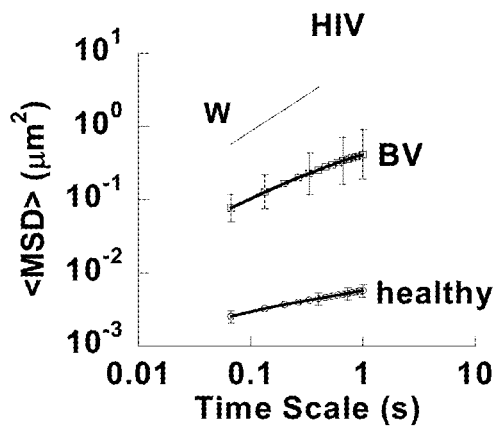

FIG. 1 shows results obtained using multiple particle tracking (a quantitative fluorescent microscopy technique) and fluorescently labeled nanoparticles or HIV virions. In FIG. 1A, the structural properties of BV-CVS are investigated. The mucins in CVS normally form a mesh or net that can sterically trap pathogens and particles. In BV-CVS, it was observed that non-adhesive nanoparticles (polyethylene glycol-coated polystyrene nanoparticles, termed mucus-penetrating particles or MPP) of similar size to bacteria (1 μm in diameter) could more rapidly diffuse in BV-CVS. Thus, FIG. 1A demonstrates the structural degradation of CVS caused by BV-associated bacteria.

FIG. 1B illustrates that BV-CVS also has reduced adhesive properties compared to CVS from women with healthy microbiota. HIV is small enough in size (~120 nm) to be able to diffuse through the pores in the mucin net in CVS, yet it was observed that healthy CVS normally traps HIV. Thus, the interactions must be adhesive in nature. However, HIV diffuses rapidly in BV-CVS, indicating reduced adhesive interactions with pathogens. It is believed that BV-associated bacteria modify mucins (e.g. enzymatic cleavage of sugar binding sites), so they are no longer adhesive to pathogens.

Figure 1C:
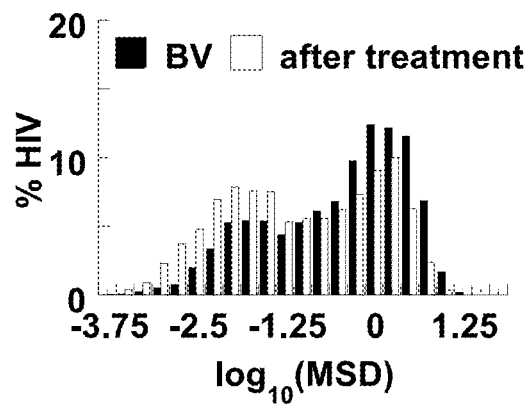
FIG. 1C is a graph of the percentage of HIV with $Log_{10}$ (MSD) values at a time scale of 1 s. Minimal difference can be seen before and after antibiotic treatment despite resolution of BV symptoms.
Figure 4A:
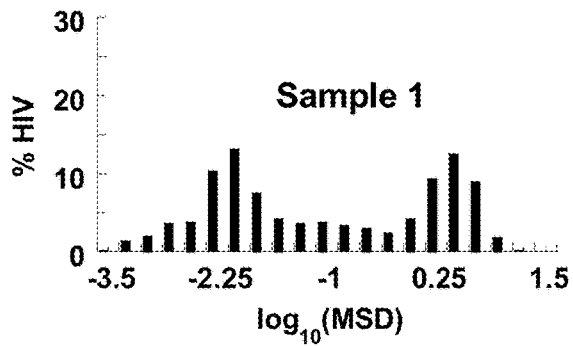
FIGS. 4A-4H are graphs of the ensemble-averaged geometric mean square displacements (<MSD>) as a function of time scale for HIV in CVS samples that do and do not trap HIV, and mixtures of trapping and non-trapping CVS samples. It was observed that mixing a non-trapping sample with a healthy trapping sample leads to complete HIV trapping in the mixture, highlighting the ability of the healthy CVS to provide a beneficial pH environment for healthy microbiota, that also provides efficient pathogen trapping.
Figure 4E:
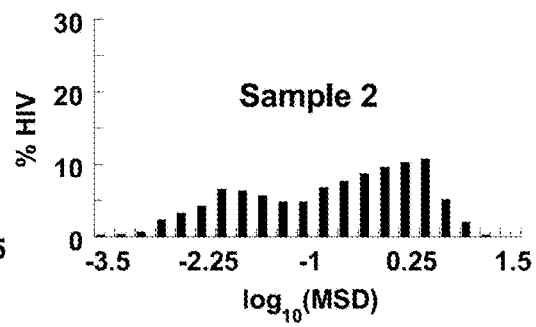
Figure 4B:
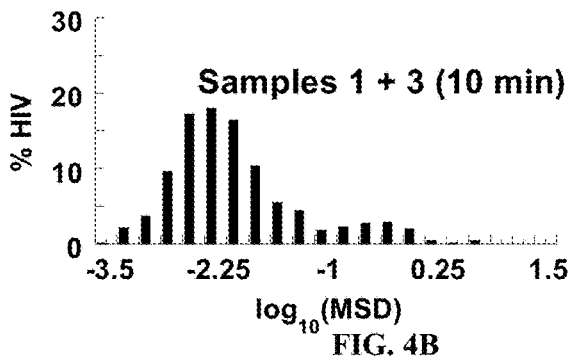
Figure 4F:
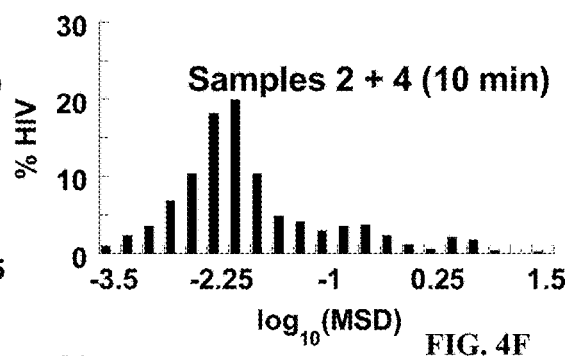
Figure 4C:
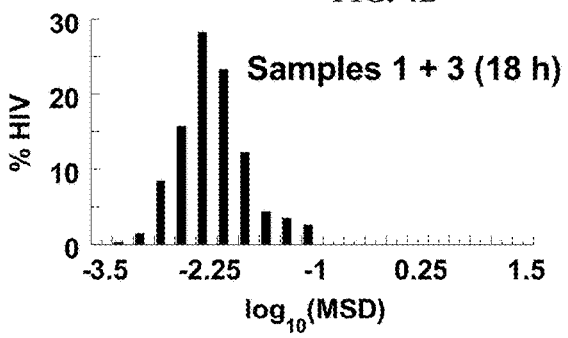
Figure 4G:
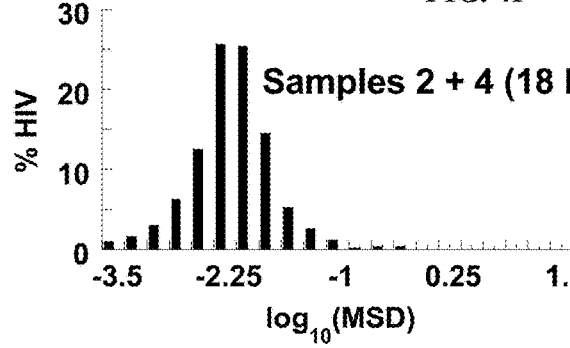
Figure 4D:
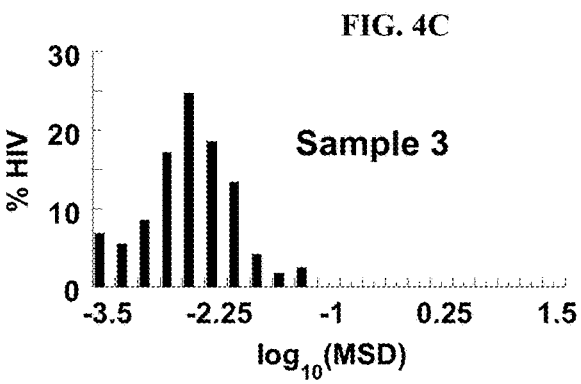
Figure 4H:
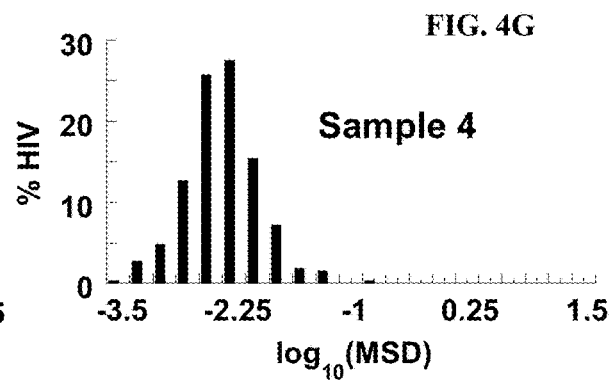

FIG. 1C illustrates that the reduced adhesion of CVS to HIV virions remains, even 1 month after antibiotic treatment for BV. It is believed that the type of bacteria most likely to colonize the vagina after BV, *Lactobacillus iners*, also produces enzymes that modify mucins. Samples were obtained from numerous women that were previously treated for BV that are *L. iners*-dominated, and HIV readily penetrates through their CVS. It appears that only CVS transplants can recolonize the vagina with healthy *lactobacillus* species, such as *Lactobacillus crispatus*. Even "successful" antibiotic treatment will lead to colonization by certain less-beneficial strains of *L. iners*, because it is the main *lactobacillus* type where certain strains can survive the BV environment, whereas *L. crispatus* is typically not present after an episode of BV.

FIG. 2 shows that colonization by certain strains of *L. iners*, which is the most likely after antibiotic treatment (if BV relapse does not occur), is associated with CVS with impaired barrier properties. FIG. 2A is an example of the heat map showing the relative abundance of bacteria in different CVS samples using 16S rRNA sequencing techniques (Dr. Jacques Ravel). As shown in FIG. 2B, a low concentration of D-lactic acid is associated with dominance by *L. iners*, which is then associated with increased mobility of HIV in the CVS. This further supports the hypothesis that even "successful" antibiotic treatment for BV (which may occur in only 50-70% of cases) is not enough to restore healthy barrier properties in CVS. Thus, only CVS transplants can successfully restore the most protective vaginal microbiota to women with BV.

Example 2: Killing of BV-Associated Bacteria in BV-CVS

Materials and Methods

Mixing experiments were performed to demonstrate killing of BV-associated bacteria in freshly obtained BV-CVS. In these experiments, the "supernatant" (the fluid containing bacteria, soluble factors, etc. after centrifuging a CVS sample to separate the large molecular weight mucin components and cells) of healthy CVS samples was mixed with BV-CVS. The mixture was then plated to determine the effectiveness of the BV-associated bacteria "killing".

Mixing experiments were performed in which CVS with pathogen trapping ability was mixed 1:1 with CVS that did not trap pathogens (one participant on hormonal contraceptives (HC), and one participant with BV).

For CVS transplants to be successful, bacteria in the "donor" sample must be in an environment that is beneficial to their survival. Lactobacilli thrive in an acidic environment with high lactic acid concentration, which is inhospitable to many other types of bacteria, including those commonly associated with BV. Thus, it is important that, upon mixing with the vaginal secretions of a woman with BV, the environment must become acidified.

Results

As shown in FIG. 3, buffer and 1% lactic acid (LA) at pH 4.5 (the vaginal pH cutoff commonly defined for BV) had little effect. In contrast, 1% lactic acid at pH 3.5 (mimicking the healthy vaginal environment) was potent at inactivating BV-associated bacteria in BV-CVS. Similarly, the supernatant of an *L. crispatus*-dominated CVS sample produced a 5-log reduction in By-associated bacteria. In contrast, the supernatant of an *L. iners*-dominated CVS sample was less effective than the supernatant from the *L. crispatus* sample or 1% LA at pH 3.5. This result supports two hypotheses: 1) healthy CVS, when mixed with BV-CVS, can sufficiently alter the local environment to both kill BV-associated bacteria and promote *lactobacillus* growth, and 2) *L. crispatus*-dominated CVS is much more potent than certain strains of *L. iners*-dominated CVS at killing BV-associated bacteria.

As shown in FIGS. 4A-4H, both CVS mixtures had moderate trapping ability immediately after mixing (MSD distribution shifted to the left, but still a small percentage of rapidly diffusing HIV), likely because of the immediate drop in pH after mixing (compare values in Tables 1 and 2 between starting samples and mixtures). The mixtures completely trapped the virus after anaerobic incubation overnight.

TABLE 1

Mobility of HIV in CVS from healthy subjects, one hormonal contraceptive receiving subject (HC), or one subject with BV.

| Sample | pH | L/D ratio | HIV tracking |
|---|---|---|---|
| 1 (HC) | 4.34 | 1.6 | mobile |
| 2 (BV) | 4.78 | 3.3 | mobile |
| 3 (healthy) | 3.93 | 0.8 | trapped |
| 4 (healthy) | 3.80 | 1.0 | trapped |

TABLE 2 pH and L/D ratio stability in CVS mixtures obtained from mixing CVS of healthy subjects (3 or 4) with that of a hormonal contraceptive receiving subject (HC) (1), or with that of a subject with BV (2).

| Mix | pH (10 min) | pH (18 h) | L/D ratio (18 h) |
|---|---|---|---|
| 1 + 3 | 4.08 | 3.57 | 0.7 |
| 2 + 4 | 3.99 | 3.71 | 1.1 |

This experiment was conducted with 3 other sample combinations, with similar results: the pH of the CVS mixture immediately after mixing was in the range ideal for *lactobacillus* growth, the CVS mixtures completely trapped virus after incubation overnight, and the L/D ratio decreased to a level similar to the healthy CVS sample.

Example 3: Effects of Lactic Acid and pH from CVS with Lactobacilli on Inactivating BV-Associated Bacteria Materials and Methods Production of Cell-Free Sterile-Filtered CVS (CF-L-CVS):

Whole CVS from individuals with lactobacilli was centrifuged at 20,000×g for 2 minutes. The collected supernatant was then spun again over a 0.2 micron spin filter.

Microdialysis:

CF-L-CVS was further pipetted into dialysis chambers and sealed with a square of 1K MWCO dialysis membrane. Chambers were floated in a medium with one of the following dialysates for 2 hours, the dialysates being saline (normal saline, 0.9% sodium chloride, pH 7), saline (containing 25 mM glycylglycine buffer and adjusted with hydrochloric acid and sodium hydroxide as needed) with pH to match the CF-L-CVS (sample pH ranges ~3-4), or saline (containing 25 mM glycylglycine buffer and adjusted with hydrochloric acid and sodium hydroxide as needed) with matching pH and matching lactic concentration as the CF-L-CVS (sample ranges 0.5-1.5% lactic acid). Both saline buffers contained adjusted sodium chloride such that each buffer had the same osmolality. The dialysis was sufficient to reduce the lactic acid concentration of CVS by ~95%, unless the dialysate was supplemented with matching concentration of lactic acid.

BV-Associated Bacteria Inactivation Assay:

BV-CVS was diluted 1:100 into one of the following media, (i) saline, (ii) CF-L-CVS, (iii) CF-L-CVS that was dialyzed against saline, (iv) CF-L-CVS that was dialyzed against saline with matching pH as the CF-L-CVS, or (v) CF-L-CVS that was dialyzed against saline with matching pH and matching lactic concentration as the CF-L-CVS. Diluted BV-CVS in a medium was incubated under anaerobic conditions at 37° C. before being plated onto *Brucella* broth 5% sheep blood plates and incubated anaerobically for 2-3 days, before colony forming units (CFUs) were counted.

Results

Figure 5A:
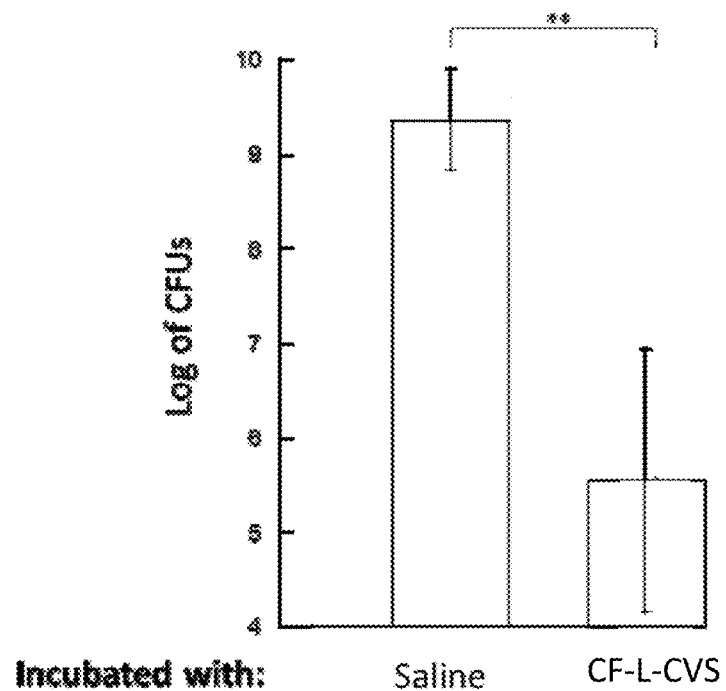
FIG. 5A is a bar graph showing numbers of colony forming units (CFUs, in log scale) formed from BV-CVS incubated with saline or with cell-free, sterile-filtered CVS (CF-L-CVS) for two hours at 37° C.
Figure 5B:
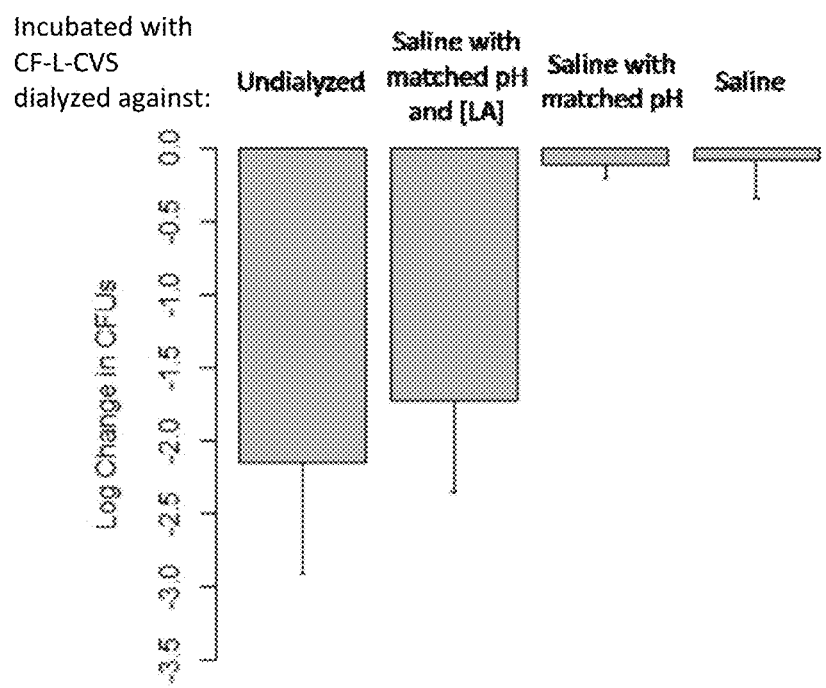
FIG. 5B is a bar graph showing reduction in the number of CFUs formed from BV-CVS incubated with undialyzed CF-L-CVS, CF-L-CVS dialyzed against saline with a matched pH, or CF-L-CVS dialyzed against saline with a matched pH and lactic acid (LA) concentration, as compared to that formed from BV-CVS incubated with saline. ** indicates p<0.01.

As shown in FIG. 5A, incubation of BV-CVS with CF-L-CVS from individuals with lactobacilli for two hours greatly reduced the number of CFUs compared to incubating BV-CVS with saline. FIG. 5B shows that dialysis of CF-L-CVS against saline prevented its ability to inactivate BV-bacteria. Since dialysis against a lactic acid saline solution retains the concentration of lactic acid in a dialyzed CVS and since lactic acid is only a potent microbicide at an acidic pH, the concentration of lactic acid and the pH of the lactic acid saline solution were matched to those of the CF-L-CVS. Despite being dialyzed, retention of lactic acid in the CF-L-CVS inactivated BV-associated bacteria similarly to undialyzed CF-L-CVS (FIG. 5B). Taken together, these results show that a high concentration of lactic acid in CVS from individuals with predominant lactobacilli microbiota inactivates BV-associated bacteria in CVS from individuals with BV.

Example 4: Transplantation of Microbiota from Normal Vaginal Mucus

Approximately one-third of all women currently have BV, a condition where the vaginal microbiota is not dominated by lactobacilli. Another one-third of women have mixed vaginal microbiota ("intermediate BV"), and only one-third of women have healthy, lactobacilli-dominated microbiota. Women with BV have >2-6-fold increased susceptibility to numerous sexually transmitted infections (STI), including HIV, herpes (HSV), gonorrhea, chlamydia, and other viral, bacterial, and protozoan pathogens. STI transmission rates from women to men are also higher if the woman has BV. Pregnant women with BV are much more susceptible to miscarriage, premature delivery, and post-partum endometriosis. Strong links have also been established between BV and increased incidence of pelvic inflammatory disease and urinary tract infections. The current clinical treatment for BV includes vaginal or oral antibiotic treatment. Current experimental methods for treating BV include lactic acid gels/washes and vaginal probiotics, and have had minimal success.

A method for transplantation of CVS from a woman with healthy vaginal microbiota to a woman with BV as a means for restoring healthy vaginal microbiota has been developed. CVS transplants should be effective to cure or reduce symptoms or severity of BV, thereby having a major impact on women's sexual and reproductive health.

Materials

Donor participants will be recruited from the Johns Hopkins hospital area. They will be asked to provide CVS samples and vaginal swabs on the initial visit for screening. If they are selected as a donor, the donor candidate will be asked to return for a more thorough screening visit that involves a routine gynecological exam, blood samples to screen for HIV and other infectious diseases, and vaginal swabs for sexually transmitted infection screening. Donor participants will agree to abstain from sexual contact between the screening visit and returning to provide a CVS sample for donation to a recipient candidate. Donor participants, due to the nature of their CVS, are at a markedly reduced risk of acquiring sexually transmitted infections.

CVS samples are obtained by insertion of an INSTEAD SOFT CUP® menstrual fluid device (as described in active protocols HIRB00000526, NA_00038105, and NA_00090758).

Methods

"Recipient" participants will be recruited from the Johns Hopkins Outpatient Center (JHOC). The recipients will be prescribed antibiotic treatment by a medical professional at the clinic. On the seventh (final) day of antibiotic treatment, the recipient will undergo a routine gynecological exam, provide vaginal swab and CVS samples, and then receive the CVS transplant.

Collected donor CVS samples are loaded into a syringe and inserted into the vagina; similar procedures are used to administer and collect fluid (cervicovaginal lavage collection) as described in active protocol NA_00036496.

Control subjects receive a standard vaginal applicator loaded with vaginal placebo gel (hydroxyethylcellulose, HEC). The recipient will be asked to remain supine for 1 h after the procedure. After the procedure, the recipients will be counseled about the benefits of condom use and the negative impacts of vaginal products on the success of the transplant. The recipients will be given journals for logging information about sexual activity and vaginal product use, as well as swabs for taking twice weekly self-samples. The recipient will be scheduled to return for 1 month and 2 month follow-up visits and instructed to bring their swab samples and journals to these visits. The follow up visits will involve a routine gynecological exam and the same sample collections as the initial visit and will take about 1 h.

Results

Definition of Treatment Failure or Participant Removal Criteria.

Donor participants will be removed from the study at any visit that they do not fulfill the criteria (bacterial flora type, lack of sexually transmitted infections, no gynecological abnormalities, no high-risk sexual behavior) for providing CVS donor samples. Recipients will not be removed from the study if they do not follow the counseled suggestions for condom use, as the impact of sexual behavior is of interest for the relative success of the CVS transplants. Even if the recipients become pregnant, the visits at month 1 and 2 are simply observational rather than interventional, and therefore do not pose a risk to the recipient participants. In the event that the recipients have BV relapse or acquire a sexually transmitted infection, they will be referred back to the clinic where they were originally treated, and will be followed through the 2 month window. There is only 1 "dose" involved in the CVS transplant procedure. If the participants have a BV relapse or acquire a sexually transmitted infection, they will be referred back to their medical provider at JHOC for treatment. CVS transplants are not intended as an ongoing therapy at this time.

Primary Outcome Variable.

The primary outcome will be whether the recipient participations are classified as having BV as assessed by standard Amsel's criteria in the clinic and by Nugent scoring at the 1 month and 2 month follow up visits.

Secondary Outcome Variables.

The secondary outcome will be the composition of the recipient participant's vaginal microbiota at the 1 month and 2 month follow-up visits, which will be determined by RNA analysis of the vaginal swabs collected.

The recipient participants can benefit by improved rates and longer duration of BV resolution, as standard antibiotic treatment often leads to relapse within a month. As such, the women that receive only standard treatment will likely have recurrent BV symptoms in addition to the numerous sexual and reproductive risks associated with BV. In contrast, a successfully CVS transplant could provide prolonged resolution of symptoms and resistance to relapse.

Example 5: Long-Term Storage and Transplantation of Cervicovaginal Secretions (CVS)

Materials

Cryoprotectant solution contains between 1% and 15% glycerol in saline.

Lactic acid-based diluent containing between about 0.5 and 1.5% lactic acid with sodium chloride and balanced to osmolality 200-300 mOsm, and a pH of between 3.0 and 4.0.

Methods

1. Cervicovaginal secretions (CVS) will be collected whole and undiluted, generally yielding between 0.2 and 1 mL of material.
2. CVS will be slow frozen. Some samples will be mixed at up to 1:1 dilution with cryoprotectant containing up to 15% glycerol and saline to improve bacterial viability upon thawing. Ideal freezing conditions will be evaluated for each "Donor's" CVS sample.
3. Upon thawing, CVS may be diluted up to a total volume of 5-50 mL with a lactic acid based diluent.
4. Diluted material may be incubated for up to 1 h at 37° C. to bring the diluted CVS mixture up to body temperature.
5. Diluted CVS mixture may be administered to the vagina using a douche bottle with spray tip, a douche bottle, or other standard vaginal applicator device.

"Donor" Identification

Donors will be screened to ensure:
1. Community dominance (>50% of overall bacterial community) of CVS by *Lactobacillus crispatus, iners, gasseri, jensenii* or other relevant vaginal *lactobacillus* species;
2. Community dominance is stable (i.e. fluctuations occurring at menstruation that recover back to similar community dominance throughout the next cycle, evaluated over 1-3 full menstrual cycles); and
3. CVS must have characteristics: pH <4, total lactic acid >0.8%, Nugent score <2, negative by Amsel's criteria.

Freezing and Thawing

The CVS from various donors were collected and frozen at various conditions described below.

The samples of frozen CVS were thawed by immersing sample tubes in 37° C. water bath for 10 minutes. The samples were then transferred to incubator set at 37° C. for 20 minutes, then diluted and plated.

Colony forming units of samples H260 and H257 (ID numbers denote individual patient samples) before freezing (Fresh), and after thawing, at a given dilution, were counted and presented in Tables 3-6 below.

Results

Data for freezing conditions suggest that each sample should be evaluated for optimal freezing conditions and use of a cryoprotectant. In some cases, CVS itself serves as the best cryoprotectant.

H260 (optimal conditions include 3.75% glycerol/saline with slow freeze).

TABLE 3

Colony forming units in a fresh H260 sample diluted by a factor of $10^8$.

| Dilution | Fresh | 7.5% glycerol/saline | 3.75% glycerol/saline | 1.875% glycerol/saline |
|---|---|---|---|---|
| $10^8$ | 286 | 5 | 302 | 237 |

TABLE 4

Colony forming units in the H260 sample after thawing and diluting by a factor of $10^8$.

| Dilution | Slow freeze 0 C. | Progressive slow freeze 0 C.; −15 C.; −80 C. | 7.5% glycerol/saline fast freeze | 3.75% glycerol/saline fast freeze | 1.875% glycerol/saline fast freeze | 1.875% glycerol/saline slow freeze |
|---|---|---|---|---|---|---|
| $10^8$ | 4 | 0 | 0 | 114 | 334 | 620 |

H257 (Optimal Conditions Appear to be Slow Freeze without Glycerol)

TABLE 5

Colony forming units in a fresh H257 sample diluted at indicated dilution factors.

| Dilution | Fresh | 7.5% glycerol |
|---|---|---|
| $10^6$ | >1000 | 600 |
| $10^7$ | 878 | 320 |
| $10^8$ | 414 | 42 |

TABLE 6

Colony forming units in the H257 sample after thawing and diluting at indicated dilution factors.

| Dilution | Slow freeze w/o glycerol | 7.5% glycerol/saline fast freeze |
|---|---|---|
| $10^6$ | 936 | 720 |
| $10^7$ | 481 | 457 |
| $10^8$ | 224 | 149 |

We claim:

1. A formulation for vaginal administration to restore normal cervicovaginal microflora in a recipient in need thereof, the formulation comprising:
    an isolated lyophilized cervicovaginal secretion,
    healthy vaginal microbiota, wherein at least 50% of the healthy vaginal microbiota is a *Lactobacillus* species typically found in the human vagina, the secretion having no evidence of sexually transmitted disease or bacterial vaginosis,
    a dissolution agent comprising between about 0.5 and 1.5% lactic acid to promote growth of the healthy vaginal microbiota, and between about 1% and 15% of a cryoprotectant to enhance the viability of the healthy vaginal microbiota relative to the viability of the healthy vaginal microbiota in the absence of the cryoprotectant, wherein the formulation is formulated for administration to the vagina of a recipient.

2. The formulation of claim 1, wherein the isolated cervicovaginal secretion has been sterile filtered and pH adjusted prior to addition of healthy vaginal microbiota.

3. The formulation of claim 1, wherein the microbiota comprises *Lactobacillus* bacteria isolated or cultured in vitro.

4. The formulation of claim 1 packaged into a dosage unit in an applicator for administration to a woman.

5. The formulation of claim 1, wherein the formulation has been frozen and thawed for administration to a woman.

6. The formulation of claim 1, wherein the cryoprotectant is selected from the group of cryoprotectants consisting of glycerol, sucrose, dextrose, polyvinylpyrrolidone (PVP), and dimethylsulfoxide (DMSO).

7. The formulation of claim 1, wherein the formulation has been spray dried or lyophilized, optionally in combination with a resuspending agent.

8. The formulation of claim 1, wherein the lactic acid is D-lactic acid.

9. The formulation of claim 1, wherein the cervicovaginal secretion comprises cervicovaginal secretions from more than one donor with vaginal microbiota dominated by *Lactobacillus*.

10. The formulation of claim 1, wherein the vaginal microbiota is dominated by *Lactobacillus* crispatus species.

11. The formulation of claim 1, wherein the dissolution agent comprises about 1% lactic acid.

* * * * *